(12) United States Patent
Uriu

(10) Patent No.: US 8,975,078 B2
(45) Date of Patent: Mar. 10, 2015

(54) METHOD FOR EXPRESSING A MOUSE OLFACTORY RECEPTOR OLFR15 ON A CELL MEMBRANE

(71) Applicant: Panasonic Corporation, Osaka (JP)

(72) Inventor: Yoshitsugu Uriu, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 153 days.

(21) Appl. No.: 13/681,894

(22) Filed: Nov. 20, 2012

(65) Prior Publication Data

US 2013/0137179 A1     May 30, 2013

Related U.S. Application Data

(63) Continuation of application No. PCT/JP2012/001784, filed on Mar. 14, 2012.

(30) Foreign Application Priority Data

Oct. 26, 2011    (JP) ................................. 2011-234874

(51) Int. Cl.
    *C12N 15/00*         (2006.01)
    *C12N 5/071*         (2010.01)
    *C07K 14/705*       (2006.01)

(52) U.S. Cl.
    CPC ............ *C12N 5/0602* (2013.01); *C07K 14/705* (2013.01)
    USPC .......................................... 435/455; 435/440

(58) Field of Classification Search
    USPC ................................................ 435/440, 455
    See application file for complete search history.

(56) References Cited

PUBLICATIONS

Katada et al. (2004, J. Neurochemistry, vol. 90, pp. 1453-1463).*
Wellerdieck et al. (1997, Chem. Senses, vol. 22, pp. 467-476).*
S. Katada et al., Structural determinants for membrane trafficking and G protein selectivity of a mouse olfactory receptor, Journal of Neurochemistry, 2004, 90, 1453-1463.
H. Saito et al., "RTP Family Members Induce Functional Expression of Mammalian Odorant Receptors," Cell, vol. 119, 679-691, Nov. 24, 2004.
P. Nef et al., "Spatial pattern of receptor expression in the olfactory epithelium," Proc. Natl. Acad. Sci. USA, vol. 89, pp. 8948-8952, Oct. 1992.
Y. Uriu et al., "Rab3-interacting Molecule γ Isoforms Lacking the Rab3-binding Domain Induce Long Lasting Currents but Block Neurotransmitter Vesicle Anchoring in Voltage-dependent P/Q-type Ca2+ Channels," The Journal of Biological Chemistry vol. 285, No. 28, pp. 21750-21767.
International Search Report issued in International Patent Application No. PCT/JP2012-001784 dated May 29, 2012.
Notification of Transmittal of Translation of the International Preliminary Report on Patentability (Chapter I), issued in PCT/JP2012/001784 on Apr. 29, 2014.

* cited by examiner

*Primary Examiner* — Anoop Singh
*Assistant Examiner* — David A Montanari
(74) *Attorney, Agent, or Firm* — McDermott Will & Emery LLP

(57) ABSTRACT

Provided is a method for effectively expressing mouse olfactory receptor Olfr15 on the cell membrane. The method includes steps of:
    bringing a cell into contact with a culture medium containing chlorpromazine; separating the culture medium from the cell so as to remove the culture medium; and incubating the cell using a culture medium which does not contain chlorpromazine to express the mouse olfactory receptor Olfr15 on the cell membrane.

4 Claims, 5 Drawing Sheets

SEQUENCE LISTING

<160> NUMBER OF SEQ ID NOS: 29

<210> SEQ ID NO 1
<211> LENGTH: 227
<212> TYPE: PRT
<213> ORGANISM: Mus musculus

<400> SEQUENCE: 1

Met Cys Lys Ser Val Thr Thr Gly Glu Trp Lys Lys Val Phe Tyr Glu
1               5                   10                  15

Lys Met Glu Glu Val Lys Pro Ala Asp Ser Trp Asp Phe Ile Ile Asp
            20                  25                  30

Pro Asn Leu Lys His Asn Val Leu Ala Pro Gly Trp Lys Gln Tyr Leu
        35                  40                  45

Glu Leu His Ala Ser Gly Arg Phe His Cys Ser Trp Cys Trp His Thr
    50                  55                  60

Trp Gln Ser Pro His Val Val Ile Leu Phe His Met Tyr Leu Asp Lys
65                  70                  75                  80

Ala Gln Arg Ala Gly Ser Val Arg Met Arg Val Phe Lys Gln Leu Cys

```
                85                  90                  95
Tyr Glu Cys Gly Thr Ala Arg Leu Asp Glu Ser Ser Met Leu Glu Glu
            100                 105                 110

Asn Ile Glu Ser Leu Val Asp Asn Leu Ile Thr Ser Leu Arg Glu Gln
        115                 120                 125

Cys Tyr Gly Glu Arg Gly His Tyr Arg Ile His Val Ala Ser Arg
    130                 135                 140

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Ala
            165                 170                 175

Thr Thr Tyr Thr Phe Ser Arg Ala Pro Ser Pro Thr Lys Pro Gln Ala
            180                 185                 190

Glu Thr Gly Ser Gly Cys Asn Phe Cys Ser Ile Pro Trp Cys Leu Phe
            195                 200                 205

Trp Ala Thr Val Leu Met Leu Ile Ile Tyr Leu Gln Phe Ser Phe Arg
    210                 215                 220

Thr Ser Val
225

<210> SEQ ID NO 2
<211> LENGTH: 26
<212> TYPE: DNA
<213> ORGANISM: Artificial
<220> FEATURE:
<223> OTHER INFORMATION: a primer for cloning RTP1S

<400> SEQUENCE: 2
tgggtcctgc ttcctcctga tcctgc                                        26

<210> SEQ ID NO 3
<211> LENGTH: 27
<212> TYPE: DNA
<213> ORGANISM: Artificial
<220> FEATURE:
<223> OTHER INFORMATION: a primer for cloning RTP1S

<400> SEQUENCE: 3
ccattcccaa gtcaggtctc acctcac                                       27

<210> SEQ ID NO 4
<211> LENGTH: 35
<212> TYPE: DNA
<213> ORGANISM: Artificial
<220> FEATURE:
<223> OTHER INFORMATION: a primer for adding EcoRI site

<400> SEQUENCE: 4
cagaattcgc caccatgtgt aagagtgtga ccaca                              35

<210> SEQ ID NO 5
<211> LENGTH: 31
<212> TYPE: DNA
<213> ORGANISM: Artificial
<220> FEATURE:
<223> OTHER INFORMATION: a primer for adding SalI site

<400> SEQUENCE: 5
gaagtcgact tagacagaag tacggaagga g                                  31

<210> SEQ ID NO 6
```

```
<211> LENGTH: 30
<212> TYPE: DNA
<213> ORGANISM: Artificial
<220> FEATURE:
<223> OTHER INFORMATION: a primer for cloning mOREG

<400> SEQUENCE: 6
ctagactctg tcagatggaa atcacagtgg                               30

<210> SEQ ID NO 7
<211> LENGTH: 30
<212> TYPE: DNA
<213> ORGANISM: Artificial
<220> FEATURE:
<223> OTHER INFORMATION: a primer for cloning mOREG

<400> SEQUENCE: 7
ttaagaagaa tagactttag tacctattat                               30

<210> SEQ ID NO 8
<211> LENGTH: 59
<212> TYPE: DNA
<213> ORGANISM: Artificial
<220> FEATURE:
<223> OTHER INFORMATION: a primer for adding Rho-tag

<400> SEQUENCE: 8
cgtgcctttc tccaacaaga cgggcgtcgt aatgactctg tcagatggaa atcacagtg   59

<210> SEQ ID NO 9
<211> LENGTH: 59
<212> TYPE: DNA
<213> ORGANISM: Artificial
<220> FEATURE:
<223> OTHER INFORMATION: a primer for adding Rho-tag

<400> SEQUENCE: 9
cgaattcatg aacgggaccg agggcccaaa cttctacgtg cctttctcca acaagacgg   59

<210> SEQ ID NO 10
<211> LENGTH: 20
<212> TYPE: PRT
<213> ORGANISM: Artificial
<220> FEATURE:
<223> OTHER INFORMATION: a Rho tag

<400> SEQUENCE: 10

Met Asn Gly Thr Glu Gly Pro Asn Phe Tyr Val Pro Phe Ser Asn Lys
1               5                   10                  15

Thr Gly Val Val
            20

<210> SEQ ID NO 11
<211> LENGTH: 26
<212> TYPE: DNA
<213> ORGANISM: Artificial
<220> FEATURE:
<223> OTHER INFORMATION: a primer for sub-clioning Rho-mOREG

<400> SEQUENCE: 11
tcccagttca attacagctc ttaagg                                   26

<210> SEQ ID NO 12
<211> LENGTH: 67
<212> TYPE: DNA
<213> ORGANISM: Artificial
```

-continued

<220> FEATURE:
<223> OTHER INFORMATION: a primer for sub-cloning Rho-mOREG

<400> SEQUENCE: 12
tgacagagtc atgaattcca gatcctcttc agagatgagt ttctgctcta cgacgcccgt    60
cttgttg                                                              67

<210> SEQ ID NO 13
<211> LENGTH: 10
<212> TYPE: PRT
<213> ORGANISM: Artificial
<220> FEATURE:
<223> OTHER INFORMATION: a myc epitope tag

<400> SEQUENCE: 13

Glu Gln Lys Leu Ile Ser Glu Glu Asp Leu
1               5                   10

<210> SEQ ID NO 14
<211> LENGTH: 35
<212> TYPE: DNA
<213> ORGANISM: Artificial
<220> FEATURE:
<223> OTHER INFORMATION: a primer for sub-cloning Rho-mOREG

<400> SEQUENCE: 14
atctggaatt catgactctg tcagatggaa atcac                               35

<210> SEQ ID NO 15
<211> LENGTH: 39
<212> TYPE: DNA
<213> ORGANISM: Artificial
<220> FEATURE:
<223> OTHER INFORMATION: a primer for sub-cloning Rho-mOREG

<400> SEQUENCE: 15
aaagtcgacc cgggattaag aagaatagac tttagtacc                           39

<210> SEQ ID NO 16
<211> LENGTH: 34
<212> TYPE: DNA
<213> ORGANISM: Artificial
<220> FEATURE:
<223> OTHER INFORMATION: a primer for cloning Olfr15

<400> SEQUENCE: 16
agaggatctg gaattcatgg aggtggacag caac                                34

<210> SEQ ID NO 17
<211> LENGTH: 34
<212> TYPE: DNA
<213> ORGANISM: Artificial
<220> FEATURE:
<223> OTHER INFORMATION: a primer for cloning Olfr15

<400> SEQUENCE: 17
ggccgcccgg gtcgactcag ctggctcctc ttcc                                34

<210> SEQ ID NO 18
<211> LENGTH: 30
<212> TYPE: PRT
<213> ORGANISM: Artificial
<220> FEATURE:
<223> OTHER INFORMATION: a Rho-tag - a myc epotope tag

<400> SEQUENCE: 18

```
Met Asn Gly Thr Glu Gly Pro Asn Phe Tyr Val Pro Phe Ser Asn Lys
 1               5                  10                  15

Thr Gly Val Val Glu Gln Lys Leu Ile Ser Glu Glu Asp Leu
             20                  25                  30

<210> SEQ ID NO 19
<211> LENGTH: 312
<212> TYPE: PRT
<213> ORGANISM: Mus musculus

<400> SEQUENCE: 19

Met Glu Val Asp Ser Asn Ser Ser Gly Ser Phe Ile Leu Met Gly
 1               5                  10                  15

Val Ser Asp His Pro His Leu Glu Ile Ile Phe Phe Ala Val Ile Leu
             20                  25                  30

Ala Ser Tyr Leu Leu Thr Leu Val Gly Asn Leu Thr Ile Ile Leu Leu
                 35                  40                  45

Ser Arg Leu Asp Ala Arg Leu His Thr Pro Met Tyr Phe Phe Leu Ser
 50                  55                  60

Asn Leu Ser Ser Leu Asp Leu Ala Phe Thr Thr Ser Ser Val Pro Gln
65                  70                  75                  80

Met Leu Lys Asn Leu Trp Gly Pro Asp Lys Thr Ile Ser Tyr Gly Gly
                 85                  90                  95

Cys Val Thr Gln Leu Tyr Val Phe Leu Trp Leu Gly Ala Thr Glu Cys
            100                 105                 110

Ile Leu Leu Val Val Met Ala Phe Asp Arg Tyr Val Ala Val Cys Arg
            115                 120                 125

Pro Leu His Tyr Met Thr Val Met Asn Pro Arg Leu Cys Trp Gly Leu
            130                 135                 140

Ala Ala Ile Ser Trp Leu Gly Gly Leu Gly Asn Ser Val Ile Gln Ser
145                 150                 155                 160

Thr Phe Thr Leu Gln Leu Pro Phe Cys Gly His Arg Lys Val Asp Asn
                165                 170                 175

Phe Leu Cys Glu Val Pro Ala Met Ile Lys Leu Ala Cys Gly Asp Thr
            180                 185                 190

Ser Leu Asn Glu Ala Val Leu Asn Gly Val Cys Thr Phe Phe Thr Val
            195                 200                 205

Val Pro Val Ser Val Ile Leu Val Ser Tyr Cys Phe Ile Ala Gln Ala
            210                 215                 220

Val Met Lys Ile Arg Ser Val Glu Gly Arg Arg Lys Ala Phe Asn Thr
225                 230                 235                 240

Cys Val Ser His Leu Val Val Phe Leu Phe Tyr Gly Ser Ala Ile
                245                 250                 255

Tyr Gly Tyr Leu Leu Pro Ala Lys Ser Ser Asn Gln Ser Gln Gly Lys
                260                 265                 270

Phe Ile Ser Leu Phe Tyr Ser Val Val Thr Pro Met Val Asn Pro Leu
            275                 280                 285

Ile Tyr Thr Leu Arg Asn Lys Glu Val Lys Gly Ala Leu Gly Arg Leu
            290                 295                 300

Leu Gly Lys Gly Arg Gly Ala Ser
305                 310

<210> SEQ ID NO 20
<211> LENGTH: 344
<212> TYPE: PRT
```

<213> ORGANISM: Artificial
<220> FEATURE:
<223> OTHER INFORMATION: Rho-myc-Olfr15

<400> SEQUENCE: 20

```
Met Asn Gly Thr Glu Gly Pro Asn Phe Tyr Val Pro Phe Ser Asn Lys
1               5                   10                  15

Thr Gly Val Val Glu Gln Lys Leu Ile Ser Glu Glu Asp Leu Glu Phe
            20                  25                  30

Met Glu Val Asp Ser Asn Ser Ser Gly Ser Phe Ile Leu Met Gly
        35                  40                  45

Val Ser Asp His Pro His Leu Glu Ile Ile Phe Phe Ala Val Ile Leu
50                  55                  60

Ala Ser Tyr Leu Leu Thr Leu Val Gly Asn Leu Thr Ile Ile Leu Leu
65                  70                  75                  80

Ser Arg Leu Asp Ala Arg Leu His Thr Pro Met Tyr Phe Phe Leu Ser
                85                  90                  95

Asn Leu Ser Ser Leu Asp Leu Ala Phe Thr Thr Ser Ser Val Pro Gln
            100                 105                 110

Met Leu Lys Asn Leu Trp Gly Pro Asp Lys Thr Ile Ser Tyr Gly Gly
        115                 120                 125

Cys Val Thr Gln Leu Tyr Val Phe Leu Trp Leu Gly Ala Thr Glu Cys
130                 135                 140

Ile Leu Leu Val Val Met Ala Phe Asp Arg Tyr Val Ala Val Cys Arg
145                 150                 155                 160

Pro Leu His Tyr Met Thr Val Met Asn Pro Arg Leu Cys Trp Gly Leu
                165                 170                 175

Ala Ala Ile Ser Trp Leu Gly Gly Leu Gly Asn Ser Val Ile Gln Ser
            180                 185                 190

Thr Phe Thr Leu Gln Leu Pro Phe Cys Gly His Arg Lys Val Asp Asn
        195                 200                 205

Phe Leu Cys Glu Val Pro Ala Met Ile Lys Leu Ala Cys Gly Asp Thr
210                 215                 220

Ser Leu Asn Glu Ala Val Leu Asn Gly Val Cys Thr Phe Phe Thr Val
225                 230                 235                 240

Val Pro Val Ser Val Ile Leu Val Ser Tyr Cys Phe Ile Ala Gln Ala
                245                 250                 255

Val Met Lys Ile Arg Ser Val Glu Gly Arg Arg Lys Ala Phe Asn Thr
            260                 265                 270

Cys Val Ser His Leu Val Val Val Phe Leu Phe Tyr Gly Ser Ala Ile
        275                 280                 285

Tyr Gly Tyr Leu Leu Pro Ala Lys Ser Ser Asn Gln Ser Gln Gly Lys
290                 295                 300

Phe Ile Ser Leu Phe Tyr Ser Val Val Thr Pro Met Val Asn Pro Leu
305                 310                 315                 320

Ile Tyr Thr Leu Arg Asn Lys Glu Val Lys Gly Ala Leu Gly Arg Leu
                325                 330                 335

Leu Gly Lys Gly Arg Gly Ala Ser
            340
```

<210> SEQ ID NO 21
<211> LENGTH: 1035
<212> TYPE: DNA
<213> ORGANISM: Artificial
<220> FEATURE:
<223> OTHER INFORMATION: a gene sequence coding for Rho-myc-Olfr15

<400> SEQUENCE: 21

```
atgaacggga ccgagggccc aaacttctac gtgcctttct ccaacaagac gggcgtcgta      60
gagcagaaac tcatctctga agaggatctg gaattcatgg aggtggacag caacagctcc     120
tctgggagct tcattctgat gggtgtctct gaccatcccc atctggagat catcttttt     180
gctgtcatcc tggcctctta cttgttgacg ctggttggga acttgaccat catcctgctt     240
tcgcgccttg atgctcggct ccacacaccc atgtacttct tcctcagcaa cctctcctct     300
ctagaccttg cctttactac cagttcagtc cctcagatgc tgaaaaattt atgggggcca     360
gacaagacaa tcagctatgg tgggtgtgta actcaactct atgttttcct ttggctgggg     420
gctactgagt gcatactgct cgtggtgatg gcatttgatc ggtatgtggc agtttgtcgg     480
cccctgcact acatgaccgt catgaatcct cgcctctgct gggggctggc tgctattagc     540
tggttgggtg gcttaggcaa ctccgtgatt cagtcaacat tcactctcca gctcccattt     600
tgcggacacc gaaaagtgga caacttcctg tgtgaggtac cgccatgat taaattggcc     660
tgtggagaca caagtctcaa tgaggcggtg ctcaatggtg tttgtaccctt cttcactgtg     720
gtcccagtaa gcgtcatcct ggtctcttac tgcttcattg tcaggcagt gatgaagatc     780
cgctctgtgg agggacgtcg aaaggctttc aatacgtgtg tctcccactt ggtggtagtg     840
tttctcttct atggctctgc gatctatggg tatctgcttc cagctaagag cagtaatcaa     900
agccaaggaa aattcatttc tctcttctac tctgtggtca cacccatggt gaatccgctc     960
atctatactc taagaaacaa agaagtgaag ggggccctgg aagattgct ggggaaagga    1020
agaggagcca gctga                                                    1035
```

<210> SEQ ID NO 22
<211> LENGTH: 684
<212> TYPE: DNA
<213> ORGANISM: Mus musculus

<400> SEQUENCE: 22

```
atgtgtaaga gtgtgaccac aggtgagtgg aagaaggtct tctacgagaa gatggaggag      60
gtgaagccag cggacagctg ggacttcatc atagacccca acctcaagca caatgtgttg     120
gcccctggct ggaagcagta cctggaactt catgcctcag gcaggttcca ctgttcctgg     180
tgctggcaca cctggcagtc accccatgta gtcatcctct tccacatgta cctggacaag     240
gctcagcgcg ctggttcggt gcgcatgcgt gtgttcaagc agctctgcta cgagtgcggt     300
acagcacggc tggatgagtc cagcatgctg gaggagaaca tcgaaagcct ggtggacaac     360
ctcatcacca gtttgcgaga gcagtgctac ggggagcgtg gtggccacta ccgcatccat     420
gtggccagcc ggcaggacaa ccggcgcaca cgcggagagt tctgcgaggc tgccaggaa     480
ggcatcgtgc actggaagcc cagtgagaag ctgctggagg aggaggcgac cacctacacc     540
ttctcccgtg ctcccagccc caccaaaccg caggctgaaa caggctcagg ctgcaacttc     600
tgctccattc cctggtgctt attttgggcc acggttttga tgctcatcat ctacctgcaa     660
ttctccttcc gtacttctgt ctaa                                           684
```

<210> SEQ ID NO 23
<211> LENGTH: 707
<212> TYPE: DNA
<213> ORGANISM: Artificial
<220> FEATURE:
<223> OTHER INFORMATION: a gene sequence coding for EcoRI-RTP1S-SalI

<400> SEQUENCE: 23

```
cagaattcgc caccatgtgt aagagtgtga ccacaggtga gtggaagaag gtcttctacg    60
agaagatgga ggaggtgaag ccagcggaca gctgggactt catcatagac cccaacctca   120
agcacaatgt gttggcccct ggctggaagc agtacctgga acttcatgcc tcaggcaggt   180
tccactgttc ctggtgctgg cacacctggc agtcacccca tgtagtcatc ctcttccaca   240
tgtacctgga caaggctcag cgcgctggtt cggtgcgcat gcgtgtgttc aagcagctct   300
gctacgagtg cggtacagca cggctggatg agtccagcat gctggaggag aacatcgaaa   360
gcctggtgga caacctcatc accagtttgc gagagcagtg ctacggggag cgtggtggcc   420
actaccgcat ccatgtggcc agccggcagg acaaccggcg acaccgcgga gagttctgcg   480
aggcctgcca ggaaggcatc gtgcactgga agcccagtga aagctgctg gaggaggagg   540
cgaccaccta caccttctcc cgtgctccca gcccaccaa accgcaggct gaaacaggct   600
caggctgcaa cttctgctcc attccctggt gcttattttg ggccacggtt ttgatgctca   660
tcatctacct gcaattctcc ttccgtactt ctgtctaagt cgacttc                 707
```

<210> SEQ ID NO 24
<211> LENGTH: 942
<212> TYPE: DNA
<213> ORGANISM: Mus musculus

<400> SEQUENCE: 24

```
atgactctgt cagatggaaa tcacagtggg gctgtgttca ccctcttggg cttctcagat    60
tatccagaat tgacaatccc tctcttttttg atatttctca ccatctacag catcactgtg   120
gtaggaaata ttggcatgat tgtcataatc agaattaatc ccaaactgca catccccatg   180
tacttctttc tcagccacct ctcttttgtg gattttttgtt attcctccat tgttgctccc   240
aagatgctgg taaatctagt tacaatgaac agaggcatat catttgtagg atgcttagtg   300
caattctttt ttttctgtac tttcgtggta actgaatctt ttctattagg agtgatggct   360
tatgacaggt ttgtggccat ccgcaaccct ctactctaca cagtggccat gtcccagagg   420
ctctgtgcca tgctggtatt gggatcctat gcttgggggg tggtatgctc cttgatactg   480
acctgctctg ccttgaatct ttctttttat ggtttcaata tgatcaacca cttttttttgt   540
gagttctcct ctctcctttc actttcacgc tctgacacat ctgtcagtca actgttgctt   600
ttcgttttttg ccactttttaa tgagattagc acactcctta tcattctctt gtcttatgtg   660
ctcattgttg ttactattct gaagatgaag tcagcaagtg gacgccgcaa agccttctcc   720
acttgtgctt cccatctgac agctataacc atcttccatg gaacaatcct attcctatac   780
tgtgtaccta actccaagaa ctccaggcat accgtaaaag tggcctctgt gttttacaca   840
gtggtgatcc ccatgctgaa tcccctaata tacagtctga gaaataagga tgtcaaggac   900
acagtaaaaa aaataatagg tactaaagtc tattcttctt aa                       942
```

<210> SEQ ID NO 25
<211> LENGTH: 973
<212> TYPE: DNA
<213> ORGANISM: Artificial
<220> FEATURE:
<223> OTHER INFORMATION: a DNA sequence modified with SalI

<400> SEQUENCE: 25

```
cgtgcctttc tccaacaaga cgggcgtcgt aatgactctg tcagatggaa atcacagtgg    60
ggctgtgttc accctcttgg gcttctcaga ttatccagaa ttgacaatcc ctctcttttt   120
```

```
gatatttctc accatctaca gcatcactgt ggtaggaaat attggcatga ttgtcataat      180
cagaattaat cccaaactgc acatccccat gtacttcttt ctcagccacc tctcttttgt      240 ggattttgt tattcctcca ttgttgctcc caagatgctg gtaaatctag ttacaatgaa       300
cagaggcata tcatttgtag gatgcttagt gcaattcttt ttttctgta ctttcgtggt      360 aactgaatct tttctattag gagtgatggc ttatgacagg tttgtggcca tccgcaaccc      420
tctactctac acagtggcca tgtcccagag gctctgtgcc atgctggtat gggatccta      480 tgcttggggg gtggtatgct ccttgatact gacctgctct gccttgaatc tttcttttta      540
tggtttcaat atgatcaacc acttttttg tgagttctcc tctctccttt cactttcacg      600
ctctgacaca tctgtcagtc aactgttgct tttcgttttt gccacttta atgagattag      660 cacactcctt atcattctct tgtcttatgt gctcattgtt gttactattc tgaagatgaa      720
gtcagcaagt ggacgccgca aagccttctc cacttgtgct tcccatctga cagctataac      780
catcttccat ggaacaatcc tattcctata ctgtgtacct aactccaaga actccaggca      840
taccgtaaaa gtggcctctg tgttttacac agtggtgatc cccatgctga atcccctaat      900
atacagtctg agaaataagg atgtcaagga cacagtaaaa aaaataatag gtactaaagt      960
ctattcttct taa                                                         973

<210> SEQ ID NO 26
<211> LENGTH: 1009
<212> TYPE: DNA
<213> ORGANISM: Artificial
<220> FEATURE:
<223> OTHER INFORMATION: a gene sequence cofing for Rho-mOREG

<400> SEQUENCE: 26
cgaattcatg aacgggaccg agggcccaaa cttctacgtg cctttctcca acaagacggg       60
cgtcgtaatg actctgtcag atggaaatca cagtggggct gtgttcaccc tcttgggctt      120
ctcagattat ccagaattga caatccctct cttttgata tttctcacca tctacagcat      180
cactgtggta ggaaatattg gcatgattgt cataatcaga attaatccca aactgcacat      240
ccccatgtac ttctttctca gccacctctc ttttgtggat ttttgttatt cctccattgt      300
tgctcccaag atgctggtaa atctagttac aatgaacaga ggcatatcat ttgtaggatg      360
cttagtgcaa ttcttttttt tctgtacttt cgtggtaact gaatcttttc tattaggagt      420
gatggcttat gacaggtttg tggccatccg caaccctcta ctctacacag tggccatgtc      480
ccagaggctc tgtgccatgc tggtattggg atcctatgct tgggggtgg tatgctcctt      540 gatactgacc tgctctgcct tgaatctttc ttttatggt ttcaatatga tcaaccactt      600
tttttgtgag ttctcctctc tcctttcact ttcacgctct gacacatctg tcagtcaact      660
gttgcttttc gttttgcca cttttaatga gattagcaca ctccttatca ttctcttgtc      720
ttatgtgctc attgttgtta ctattctgaa gatgaagtca gcaagtggac gccgcaaagc      780
cttctccact tgtgcttccc atctgacagc tataaccatc ttccatggaa caatcctatt      840
cctatactgt gtacctaact ccaagaactc caggcatacc gtaaaagtgg cctctgtgtt      900
ttacacagtg gtgatcccca tgctgaatcc cctaatatac agtctgagaa ataaggatgt      960
caaggacaca gtaaaaaaaa taataggtac taaagtctat tcttcttaa                 1009

<210> SEQ ID NO 27
<211> LENGTH: 1135
<212> TYPE: DNA
```

```
<213> ORGANISM: Artificial
<220> FEATURE:
<223> OTHER INFORMATION: a gene sequence coding for Rho-myc-mOREG

<400> SEQUENCE: 27
tcccagttca attacagctc ttaaggctag agtacttaat acgactcact ataggctagc    60
ctcgaatgaa cgggaccgag ggcccaaact tctacgtgcc tttctccaac aagacgggcg   120
tcgtaatgac tctgtcagca acaagacggg cgtcgtagag cagaaactca tctctgaaga   180
ggatctggaa ttcatgactc tgtcagatgg aaatcacagt ggggctgtgt tcaccctctt   240
gggcttctca gattatccag aattgacaat ccctctcttt ttgatatttc tcaccatcta   300
cagcatcact gtggtaggaa atattggcat gattgtcata atcagaatta atcccaaact   360
gcacatcccc atgtacttct ttctcagcca cctctctttt gtggattttt gttattcctc   420
cattgttgct cccaagatgc tggtaaatct agttacaatg aacagaggca tatcatttgt   480
aggatgctta gtgcaattct tttttttctg tactttcgtg gtaactgaat cttttctatt   540
aggagtgatg gctatgaca ggtttgtggc catccgcaac cctctactct acacagtggc   600
catgtcccag aggctctgtg ccatgctggt attgggatcc tatgcttggg gggtggtatg   660
ctccttgata ctgacctgct ctgccttgaa tctttctttt tatggtttca atatgatcaa   720
ccactttttt tgtgagttct cctctctcct ttcactttca cgctctgaca catctgtcag   780
tcaactgttg cttttcgttt tgccactttt taatgagatt agcacactcc ttatcattct   840
cttgtcttat gtgctcattg ttgttactat tctgaagatg aagtcagcaa gtggacgccg   900
caaagccttc tccacttgtg cttcccatct gacagctata accatcttcc atggaacaat   960
cctattccta tactgtgtac ctaactccaa gaactccagg cataccgtaa aagtggcctc  1020
tgtgttttac acagtggtga tccccatgct gaatccccta atatacagtc tgagaaataa  1080
ggatgtcaag gacacagtaa aaaaaataat aggtactaaa gtctattctt cttaa        1135

<210> SEQ ID NO 28
<211> LENGTH: 971
<212> TYPE: DNA
<213> ORGANISM: Artificial
<220> FEATURE:
<223> OTHER INFORMATION: A gene coding for EcoRI-Olfr15-SalI

<400> SEQUENCE: 28
agaggatctg gaattcatgg aggtggacag caacagctcc tctgggagct tcattctgat    60
gggtgtctct gaccatcccc atctggagat catctttttt gctgtcatcc tggcctctta   120
cttgttgacg ctggttggga acttgaccat catcctgctt tcgcgccttg atgctcggct   180
ccacacaccc atgtacttct tcctcagcaa cctctcctct ctagaccttg cctttactac   240
cagttcagtc cctcagatgc tgaaaaattt atggggggcca gacaagacaa tcagctatgg   300
tgggtgtgta actcaactct atgttttcct ttggctgggg gctactgagt gcatactgct   360
cgtggtgatg gcatttgatc ggtatgtggc agtttgtcgg cccctgcact acatgaccgt   420
catgaatcct cgcctctgct gggggctggc tgctattagc tggttgggtg gcttaggcaa   480
ctccgtgatt cagtcaacat tcactctcca gctcccattt tgcggacacc gaaaagtgga   540
caacttcctg tgtgaggtac ccgccatgat taaattggcc tgtggagaca caagtctcaa   600
tgaggcggtg ctcaatggtg tttgtacctt cttcactgtg gtcccagtaa gcgtcatcct   660
ggtctcttac tgcttcattg ctcaggcagt gatgaagatc cgctctgtgg agggacgtcg   720
aaaggctttc aatacgtgtg tctcccactt ggtggtagtg tttctcttct atggctctgc   780
```

```
gatctatggg tatctgcttc cagctaagag cagtaatcaa agccaaggaa aattcatttc    840
tctcttctac tctgtggtca cacccatggt gaatccgctc atctatactc taagaaacaa    900
agaagtgaag ggggccctgg gaagattgct ggggaaagga agaggagcca gctgagtcga    960
cccgggcggc c                                                         971

<210> SEQ ID NO 29
<211> LENGTH: 139
<212> TYPE: DNA
<213> ORGANISM: Artificial
<220> FEATURE:
<223> OTHER INFORMATION: a gene coding for Rho-myc

<400> SEQUENCE: 29
gctagcctcg aatgaacggg accgagggcc caaacttcta cgtgcctttc tccaacaaga     60
cgggcgtcgt aatgactctg tcagcaacaa gacgggcgtc gtagagcaga aactcatctc    120
tgaagaggat ctggaattc                                                 139
```

METHOD FOR EXPRESSING A MOUSE OLFACTORY RECEPTOR OLFR15 ON A CELL MEMBRANE

CROSS-REFERENCE TO RELATED APPLICATIONS

This is a continuation application of International Application No. PCT/JP2012/001784, with an international filing date of Mar. 14, 2012, which claims priority of Japanese Patent Application No. 2011-234874, filed on Oct. 26, 2011, the entire contents of each of which are incorporated herein by reference.

The Sequence listing in "SEQUENCE LISTING.TXT" created on Feb. 8, 2012 and being 22.1KB in size is incorporated by reference and is identical to the sequence information in the instant application.

BACKGROUND OF THE INVENTION

Technical Field

The technical field relates to a method for expressing a mouse olfactory receptor Olfr15 on a cell membrane.

An olfactory receptor is a trimeric G protein-coupled receptor (hereinafter, referred to as "GPCR"). For example, the olfactory receptor is one kind of trimeric G protein-coupled seven-transmembrane receptors.

FIG. 5 shows a mechanism in which an odor molecule stimulus to a cell membrane is converted into an electrical signal.

The olfactory receptor is a membrane protein which is expressed on the cell membrane. The cell membrane is mainly composed of a lipid bilayer membrane. The lipid bilayer membrane has a two layer structure, each consisting of phospholipid molecules lined with a high density. This lipid bilayer membrane is schematically shown in the center of FIG. 5. In FIG. 5, the outside of the cell is above the upper part of the lipid bilayer membrane and the inside of the cell is below the lower part of the lipid bilayer membrane. The trimeric G protein is placed in the vicinity of the olfactory receptor.

The trimeric G protein is a heterotrimer composed of an alpha subunit (Gαolf), a beta-subunit (Gβ), and a gamma subunit (Gγ). The cell contains adenylate cyclase. In FIG. 5, the adenylate cyclase is referred to as "AC". The adenylate cyclase is a transmembrane-type protein. A protein RTP1S (SEQ ID NO: 01, Gen Bank Accession No: EU070411) assists the olfactory receptors to be expressed in the cell membrane, but is not directly associated with the mechanism shown in FIG. 5.

Next, the mechanism is described in further detail. The odor molecule binds to the olfactory receptor. The binding separates the trimeric G protein into the alpha subunit (Gαolf) and a beta—gamma complex. The beta-gamma complex consists of the subunit Gβ and the subunit Gγ. The separated Gαolf activates the adenylate cyclase (AC). The activated adenylate cyclase (AC) converts adenosine triphosphate (ATP) into cyclic adenosine monophosphate (cAMP).

The cyclic adenosine monophosphate (cAMP) activates an ion channel, for example, a cyclic nucleotide gated ion channel (CNG). The activation allows an ion to be transported from the inside of the cell to the outside of the cell, or from the outside of the cell to the inside of the cell. The degree of the transport of the ion can be measured as an electric signal.

The mouse olfactory receptors include various olfactory receptors depending on an odor molecule to be recognized. An example of the mouse olfactory receptor is a mouse eugenol olfactory receptor mOREG, a mouse olfactory receptor Olfr168, a mouse olfactory receptor Olfr15, or a mouse olfactory receptor Olfr609.

The mouse eugenol olfactory receptor mOREG recognizes eugenol. In other words, the mouse eugenol olfactory receptor mOREG is stimulated by eugenol. Eugenol serves as an odor molecule with regard to the mouse eugenol olfactory receptor mOREG. The mouse eugenol olfactory receptor mOREG is referred to as a mouse olfactory receptor Olfr73.

The mouse olfactory receptor Olfr168 recognizes 2-pentanone. In other words, the mouse olfactory receptor Olfr168 is stimulated by 2-pentanone. 2-pentanone serves as an odor molecule with regard to the mouse olfactory receptor Olfr168.

The mouse olfactory receptor Olfr15 recognizes cyclohexanone. In other words, the mouse olfactory receptor Olfr15 is stimulated by cyclohexanone. Cyclohexanone serves as an odor molecule with regard to the mouse olfactory receptor Olfr15.

The mouse olfactory receptor Olfr609 recognizes vanillic acid. In other words, the mouse olfactory receptor Olfr609 is stimulated by vanillic acid. The vanillic acid serves as an odor molecule with regard to the mouse olfactory receptor Olfr609.

Non Patent Literature 1 discloses a method for expressing an odorant receptor on a cell membrane by using a receptor-transporting protein (hereinafter, referred to as "RTP") such as RTP1S.

For example, cells are transfected with a vector containing a gene sequence coding for an olfactory receptor and with a vector containing a gene sequence coding for the RTP. These cells are incubated to express the olfactory receptor on the cell membrane.

CITATION LIST

Non Patent Literature 1

Saito, H., M. Kubota, et al. (2004). "RTP family members induce functional expression of mammalian odorant receptors." Cell 119(5): 679-691.

SUMMARY

As demonstrated in the Comparative Example 1, which is described later, even when cells were transfected with a gene sequence coding for the mouse olfactory receptor Olfr15 and with a gene sequence coding for the receptor-transporting protein, the mouse olfactory receptor Olfr15 was not efficiently expressed on the cell membrane thereof.

One non-limiting and exemplary embodiment provides a method for expressing the mouse olfactory receptor Olfr15 on the cell membrane efficiently.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: A method for expressing a mouse olfactory receptor Olfr15 on the cell membrane, the method including steps of:

(a) bringing a cell into contact with a culture medium containing chlorpromazine; wherein the cell is transfected with a vector coding for the mouse olfactory receptor Olfr15 and coding for a receptor-transporting protein;

(b) after the step (a), separating the culture medium from the cell so as to remove the culture medium;

(c) after the step (b), incubating the cell using a culture medium which does not contain chlorpromazine to express the mouse olfactory receptor Olfr15 on the cell membrane.

The present disclosure provides a method for expressing the mouse olfactory receptor Olfr15 on the cell membrane efficiently.

DETAILED DESCRIPTION

The embodiment of the present disclosure is described below.

The mouse olfactory receptor Olfr15 consists of the amino acid sequence represented by SEQ ID NO: 19. As long as the mouse olfactory receptor Olfr15 is expressed efficiently on the cell membrane, the N-terminal of the mouse olfactory receptor Olfr15 can be modified with an amino acid sequence. An example of this amino acid sequence is the amino acid sequence (SEQ ID NO: 18) including the Rho-tag (SEQ ID NO: 10) and the myc epitope tag (SEQ ID NO: 13). A linker may be interposed between the Rho-tag (SEQ ID NO: 10) and the myc epitope tag (SEQ ID NO: 13). Similarly, the C-terminal of the mouse olfactory receptor Olfr15 also can be modified with an amino acid sequence, as long as the mouse olfactory receptor Olfr15 is expressed efficiently on the cell membrane.

(Step (a))

Figure 4:
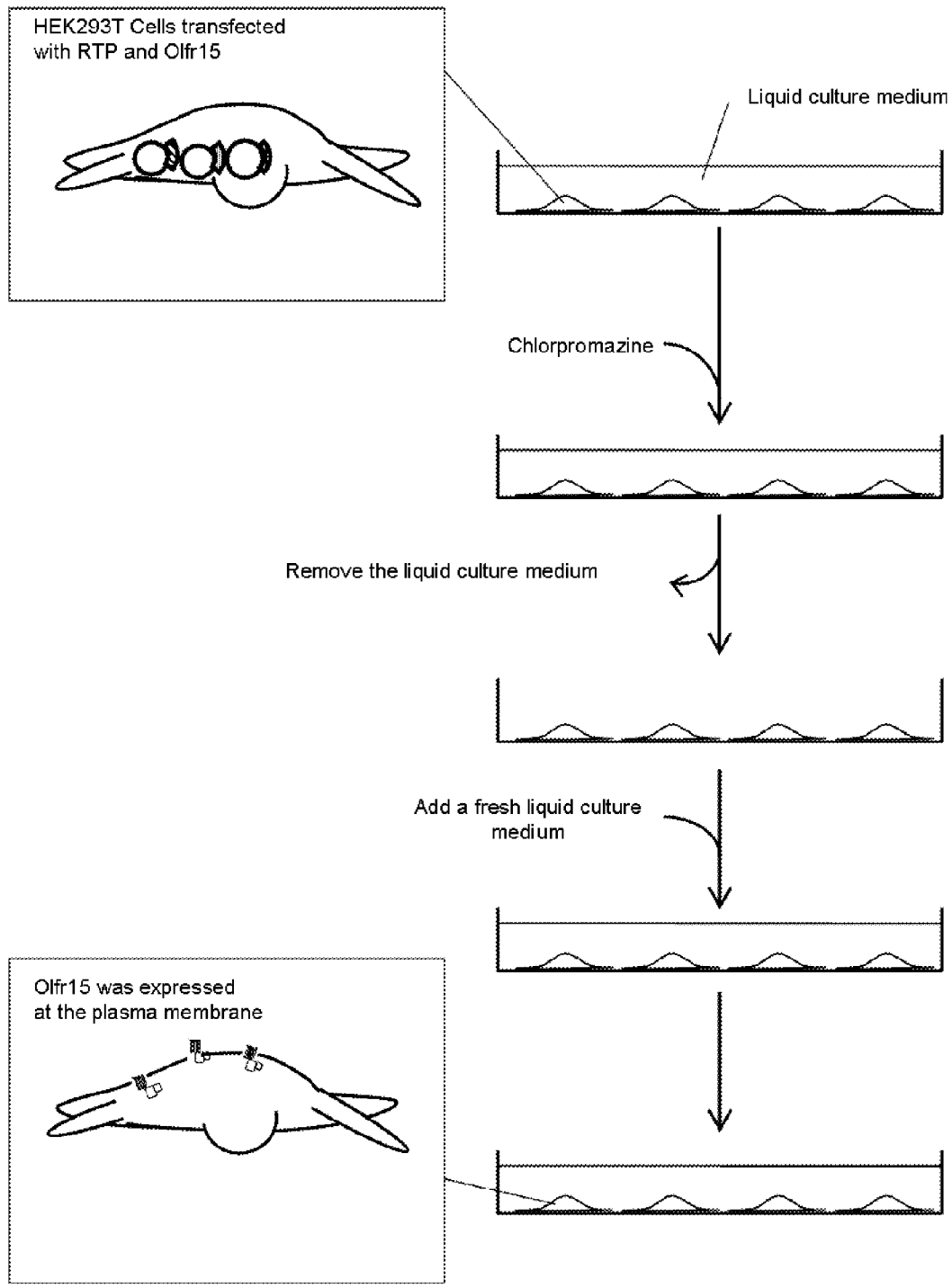
FIG. 4 schematically shows a procedure of the present disclosure.
Figure 5:
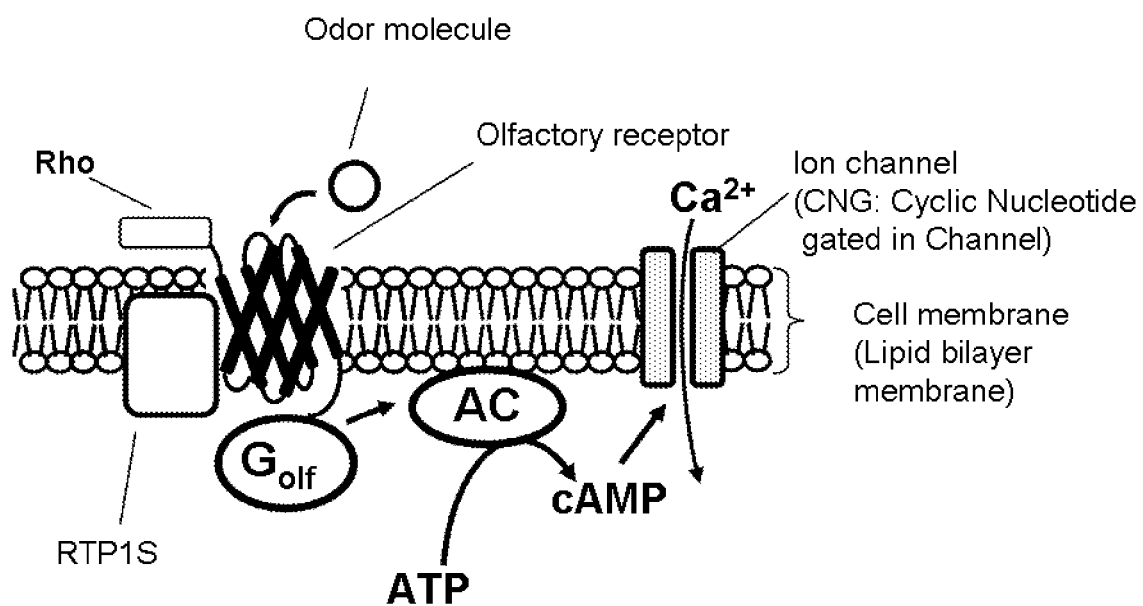
FIG. 5 shows a mechanism that a stimulus of an odor molecule to a cell membrane is converted into an electric signal.

As shown in FIG. 4, cells are brought into contact with a culture medium containing chlorpromazine. Optionally, a liquid culture medium is used. These cells have been transfected with a vector coding for the mouse olfactory receptor Olfr15 and coding for the receptor-transporting protein, as described later.

For example, the liquid culture medium containing chlorpromazine is added into a vessel containing these cells. An example of the cell is HEK293T cell.

First, after a culture fluid containing the transfected HEK293T cells is added into the vessel, the culture fluid is removed. The HEK293T cells are known to adhere spontaneously to the inner wall of the vessel in the vessel containing the culture fluid. Accordingly, as shown in the uppermost part of FIG. 4, the HEK293T cells are left on the inner wall of the vessel after the removal of the culture fluid. A liquid culture medium containing chlorpromazine is added to this vessel.

Alternatively, the liquid medium containing chlorpromazine and the cells may be mixed so as to bring the cells into contact with the liquid culture medium containing chlorpromazine.

Before the step (a), the cells are transfected with a vector coding for the mouse olfactory receptor Olfr15 and coding for the receptor-transporting protein. The vector including a gene sequence coding for the mouse olfactory receptor Olfr15 and coding for the receptor-transporting protein is introduced into the cells. One vector may include both the gene sequence coding for the mouse olfactory receptor Olfr15 and the gene sequence coding for the receptor-transporting protein. Instead of this, a first vector including the gene sequence coding for the mouse olfactory receptor Olfr15 and a second vector including the gene sequence coding for the receptor-transporting protein may be introduced into the cells. An example of the vector is a plasmid or a bacteriophage.

An example of the receptor-transporting protein is a protein RTP1S represented by SEQ ID NO: 01.

(Step (b))

After step (a), the liquid culture medium is separated from the cells to remove the liquid culture medium. As shown in FIG. 4, when the HEK293T cells are used, the culture fluid is removed from the vessel. The liquid culture medium may be separated from the cells by filtration or by centrifugal separation so as to remove the liquid culture medium.

(Step (c))

After step (b), the cells are brought into contact with a culture medium which does not contain chlorpromazine. For example, the cells may be immersed in a liquid culture medium which does not contain chlorpromazine. As shown in FIG. 4, when the HEK293T cells are used, the liquid culture medium not containing chlorpromazine is added to the vessel. Alternatively, the liquid culture medium not containing chlorpromazine may be mixed with the cells to immerse the cells in the liquid medium not containing chlorpromazine.

Thus, the liquid culture medium containing chlorpromazine is substituted with the liquid medium which does not contain chlorpromazine. In other words, the culture medium used in step (a) is exchanged with the culture medium which does not contain chlorpromazine.

Subsequently, the cells are incubated to express the mouse olfactory receptor Olfr15 on the cell membrane thereof.

Generally, when cells are incubated, proteins are usually expressed in the cells. However, in the present disclosure, the expressed mouse olfactory receptor Olfr15 is localized in the cell membrane.

Examples of the additional aspect of the present disclosure are as follows.

1st aspect: A method for expressing a mouse olfactory receptor Olfr15 on the cell membrane, the method including steps of:

(a) bringing a cell into contact with a culture medium containing chlorpromazine; wherein
the cell is transfected with a vector coding for the mouse olfactory receptor Olfr15 and coding for a receptor-transporting protein;

(b) after the step (a), separating the culture medium from the cell so as to remove the culture medium;

(c) after the step (b), incubating the cell using a culture medium which does not contain chlorpromazine to express the mouse olfactory receptor Olfr15 on the cell membrane.

2nd aspect: In the method according to the 1st aspect, in the step (a), a vector coding for the mouse olfactory receptor Olfr15 and a vector coding for the receptor-transporting protein may be used.

3rd aspect: In the method according to the 1st aspect, in the step (a), a vector coding for both of the mouse olfactory receptor Olfr15 and the receptor-transporting protein may be used.

4th aspect: In the method according to the 1st aspect, in the step (a), the concentration of the chlorpromazine may be not less than 10 μg/ml and not more than 25 μg/ml.

5th aspect: In the method according to the 1st aspect, the cell may be left at rest between the step (a) and the step (b).

6th aspect: In the method according to the 1st aspect, the mouse olfactory receptor Olfr15 may comprise of an amino acid sequence represented by SEQ ID NO: 19.

7th aspect: In the method according to the 6th aspect, the N-terminal of the mouse olfactory receptor Olfr15 may be modified with an amino acid sequence (SEQ ID NO: 18).

EXAMPLES

Examples for supporting an exemplary embodiment are described below.

Example 1

Table 1 shows the primers used in the example 1.

TABLE 1

| Primer Name | SEQ ID NO | Sequence |
|---|---|---|
| Primer 1 | SEQ ID NO: 02 | tgggtcctgcttcctcctgatcctgc |
| Primer 2 | SEQ ID NO: 03 | ccattcccaagtcaggtctcacctcac |
| Primer 3 | SEQ ID NO: 04 | cagaattcgccaccatgtgtaagagtgtgaccaca |
| Primer 4 | SEQ ID NO: 05 | gaagtcgacttagacagaagtacggaaggag |
| Primer 5 | SEQ ID NO: 16 | agaggatctggaattcatggaggtggacagcaac |
| Primer 6 | SEQ ID NO: 17 | ggccgcccgggtcgactcagctggctcctcttcc |
| Primer 7 | SEQ ID NO: 06 | ctagactctgtcagatggaaatcacagtgg |
| Primer 8 | SEQ ID NO: 07 | ttaagaagaatagactttagtacctattat |
| Primer 9 | SEQ ID NO: 08 | cgtgcctttctccaacaagacgggcgtcgtaatgactctgtcagatggaaatcacagtg |
| Primer 10 | SEQ ID NO: 09 | cgaattcatgaacgggaccgagggcccaaacttctacgtgcctttctccaacaagacgg |
| Primer 11 | SEQ ID NO: 11 | tcccagttcaattacagctcttaagg |
| Primer 12 | SEQ ID NO: 12 | tgacagagtcatgaattccagatcctcttcagagatgagtttctgctctacgacgcccgtcttgttg |
| Primer 13 | SEQ ID NO: 14 | atctggaattcatgactctgtcagatggaaatcac |
| Primer 14 | SEQ ID NO: 15 | aaagtcgacccgggattaagaagaatagactttagtacc |

(Preparation of Plasmid (RTP1S))

Figure 1:
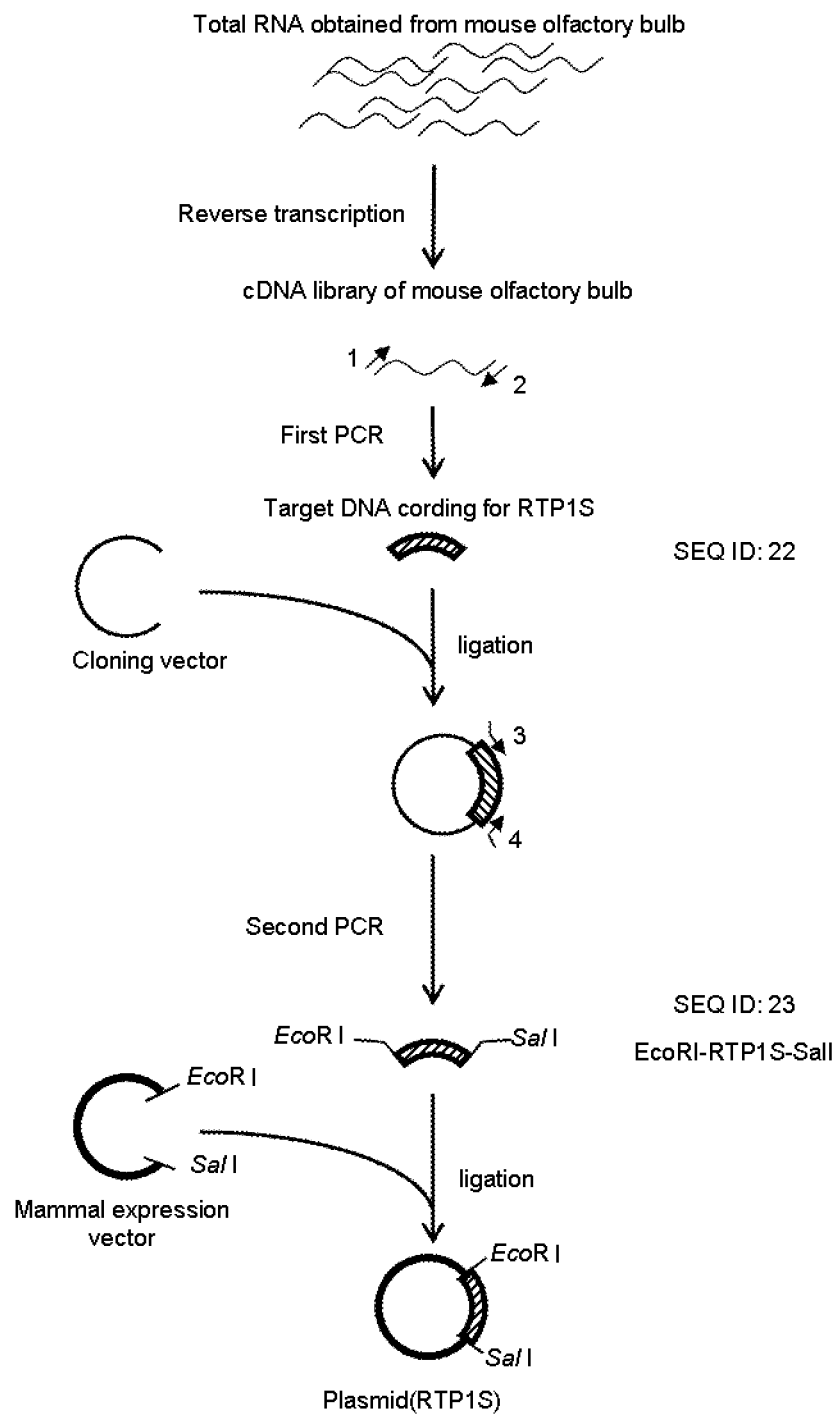
FIG. 1 shows a procedure for preparing a plasmid (RTP1S).

As shown in FIG. 1, a plasmid for expressing the RTP1S (hereinafter, referred to as "RTP1S") was prepared as below.

First, total RNAs were prepared from a mouse olfactory receptor in accordance with the method disclosed in Non Patent Literature 2.

Non Patent Literature 2

Y. Uriu et. al., "Rab3-interacting Molecule γ Isoforms Lacking the Raba-binding Domain Induce Long Lasting Currents but Block Neurotransmitter Vesicle Anchoring in Voltage-dependent P/Q-type $Ca^{2+}$ Channels.", Journal of Biological Chemistry 285(28): 21750-21767.

Then, a cDNA library of the mouse olfactory receptor was obtained from the total RNAs by a reverse transcription reaction.

A target DNA sequence coding for the RTP1S included in the cDNA library was amplified by a PCR method using the primer 1 (SEQ ID NO: 02) and the primer 2 (SEQ ID NO: 03).

Subsequently, the target DNA sequence (SEQ ID NO: 22) coding for the RTP1S was ligated into a cloning vector.

The target DNA sequence coding for the RTP1S was amplified by a PCR method using the primer 3 (SEQ ID NO: 04) and the primer 4 (SEQ ID NO: 05). The primer 3 (SEQ ID NO: 04) and the primer 4 (SEQ ID NO: 05) had restriction enzyme sites EcoRI and SalI, respectively. Thus, obtained was the target DNA sequence (SEQ ID NO: 23) having the restriction enzyme sites EcoRI and SalI at the 5'-end and the 3'-end thereof, respectively. Hereinafter, this DNA sequence is referred to as "EcoRI-RTP1S-SalI".

The target DNA sequence was ligated into a mammal expression vector. This mammal expression vector had been treated with restriction enzymes EcoRI and SalI in advance. In this way, the plasmid (RTP1S) was prepared.

(Preparation of the Plasmid (Rho-myc-Olfr15))

Figure 2:
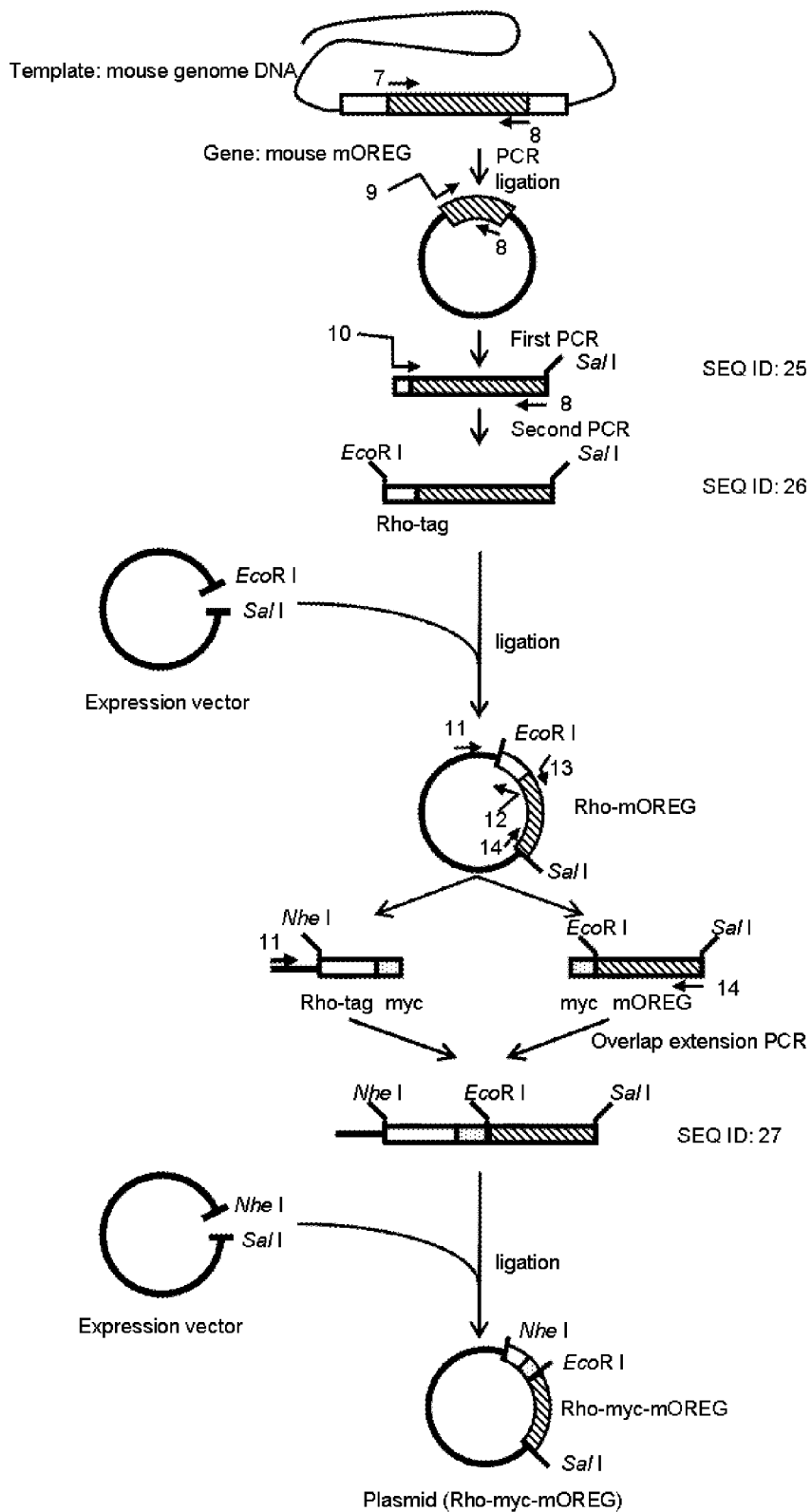
FIG. 2 shows a procedure for preparing a plasmid (Rho-myc-mOREG).
Figure 3:
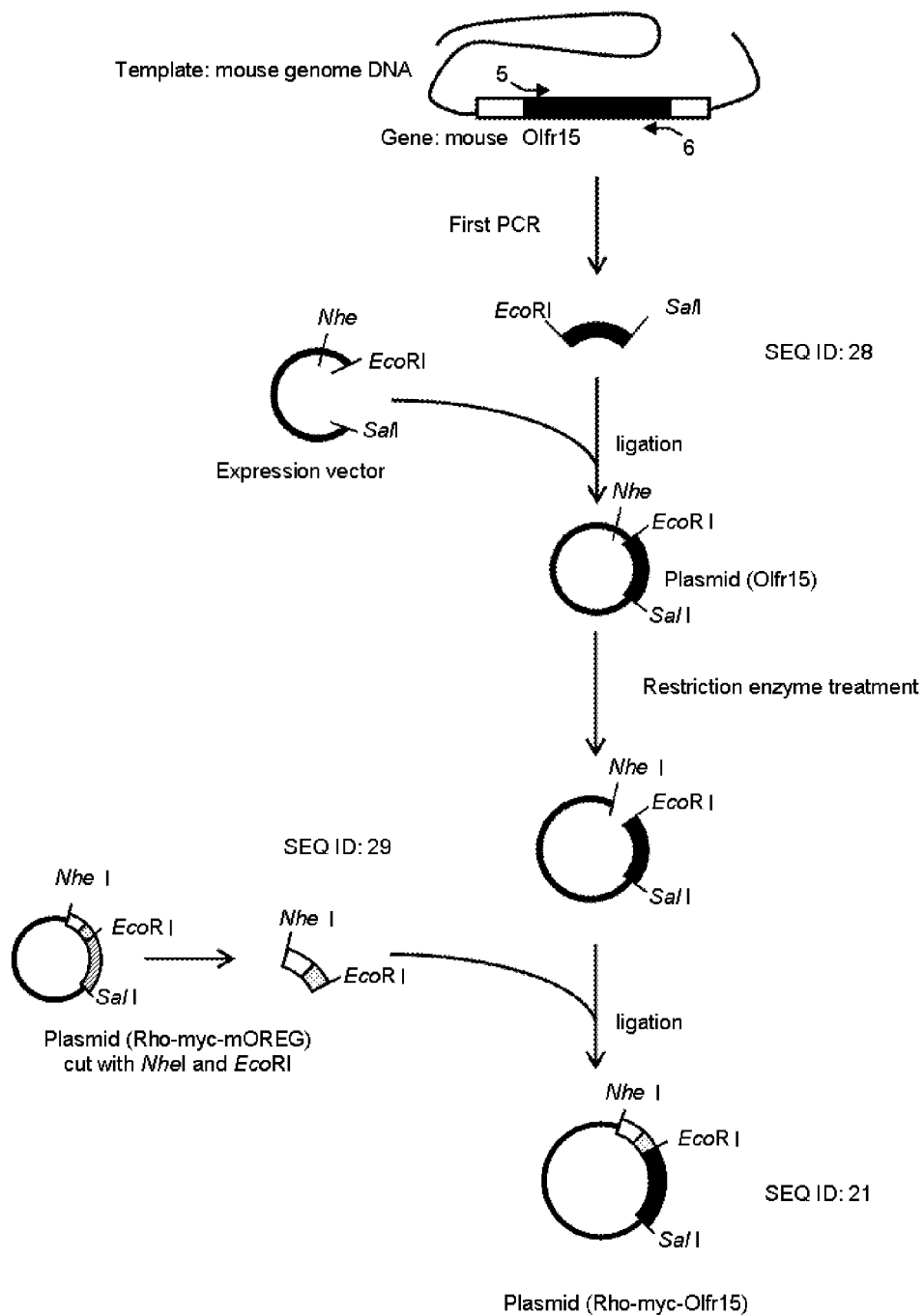
FIG. 3 shows a procedure for preparing a plasmid (Rho-myc-Olfr15).

As shown in FIG. 2 and FIG. 3, a plasmid for expressing Olfr15 (hereinafter, referred to as "plasmid (Rho-myc-Olfr15)" was prepared as below.

First, a gene (GenBank Registration Number: AB061228.1, SEQ ID NO: 24) coding for the mOREG was amplified by a PCR method using a mouse genomic DNA as a template. In this PCR method, the primer 7 (SEQ ID NO: 06) and the primer 8 (SEQ ID NO: 07) were used. The amplified gene was ligated into a cloning plasmid so as to clone the gene coding for the mOREG.

Then, the gene sequence coding for the Rho tag was added to the 5'-end of the gene coding for the mOREG by a PCR method. Since the gene sequence coding for the Rho tag (SEQ ID NO: 10) has sixty bases, the addition of the Rho tag (SEQ ID NO: 10) was divided into the following two steps (i.e., the first step and the second step).

In the first step, a PCR reaction was conducted by using the above-mentioned plasmid coding for the mOREG, the primer 8 (SEQ ID NO: 07), and the primer 9 (SEQ ID NO: 08) so as to obtain a gene fragment (SEQ ID NO: 25) in which thirty-one bases was added to the 5'-end of the gene coding for mOREG. The primer 9 (SEQ ID NO: 08) had the thirty-one bases.

Similarly, in the second step, a PCR reaction was conducted by using the gene fragment obtained in the first step, the primer 8 (SEQ ID NO: 07), and the primer 10 (SEQ ID NO: 09) so as to add the additional 29 bases to the 5'-end. The primer 10 (SEQ ID NO: 09) had the additional 29 bases. The primer 10 (SEQ ID NO: 09) also had a restriction enzyme site EcoRI.

In this way, the base sequence (60 bases) coding for the Rho tag (SEQ ID NO: 10) was added to the 5'-end of the mOREG gene so as to obtain the Rho-mOERG gene fragment (SEQ ID NO: 26). This Rho-mOERG gene fragment (SEQ ID NO: 26) was ligated into EcoRI/SalI sites of a mammal expression plasmid. In this way, the plasmid (Rho-mOREG) was obtained.

Two gene fragments were amplified by using a plasmid (Rho-mOREG) and two sets of primers.

The one gene fragment was amplified by a PCR method using the plasmid (Rho-mOREG), the primer 11 (SEQ ID NO: 11), and the primer 12 (SEQ ID NO: 12). The primer 12 (SEQ ID NO: 12) had the antisense strand of the gene sequence coding for the myc epitope tag (SEQ ID NO: 13) and had a restriction enzyme site EcoRI. In this way, amplified was the one gene fragment where the antisense strand of the gene sequence coding for the myc epitope tag (SEQ ID NO: 13) was added to the 3'-end of the Rho tag.

The other gene fragment was amplified by a PCR method using the plasmid (Rho-mOREG), the primer 13 (SEQ ID NO: 14), and the primer 14 (SEQ ID NO: 15). The primer 13 (SEQ ID NO: 14) had a part of the myc epitope tag and a restriction enzyme site EcoRI. In this way, the other gene fragment was amplified where the part of the gene sequence coding for the myc epitope tag (SEQ ID NO: 13) was added to the 5'-end of the gene coding for the mOREG.

These two gene fragments thus amplified were mixed. These two gene fragments were connected by an overlap extension PCR method using the primer 11 (SEQ ID NO: 11) and the primer 14 (SEQ ID NO: 15). The connected gene fragments (SEQ ID NO: 27) were ligated into a mammal expression plasmid which had been treated with restriction enzymes NheI and SalI in advance. In this way, as shown in the bottom of FIG. 2, the plasmid (Rho-myc-mOREG) was obtained.

As shown in FIG. 3, the gene fragment (GenBank registration number: BC146531) coding for the Olfr15 was amplified with a PCR method using mouse genomic DNAs as a template. In this PCR method, the primer 5 (SEQ ID NO: 16) and the primer 6 (SEQ ID NO: 17) were used. The primer 5 and the primer 6 had restriction enzyme sites EcoRI and San, respectively. In this way, the gene fragment (SEQ ID NO: 28) was obtained.

This gene fragment was ligated into a cloning plasmid to obtain a plasmid. This cloning plasmid had been treated with restriction enzymes EcoRI and Sail in advance. This cloning plasmid had a restriction enzyme site NheI.

This plasmid was treated with restriction enzymes NheI and EcoRI.

On the other hand, the plasmid (Rho-myc-mOREG) was treated with restriction enzymes NheI and EcoRI to obtain the gene fragment (SEQ ID NO: 29) coding for the Rho-tag—the myc epitope tag. This gene fragment (SEQ ID NO: 29) was ligated into the plasmid. In this way, the plasmid (Rho-myc-Olfr15) was obtained. The plasmid (Rho-myc-Olfr15) contained the gene sequence (SEQ ID NO: 21).

(Preparation of Cells)
The liquid culture medium containing HEK293T cells was added into a Petri dish. The HEK293T cells adhered spontaneously to the inner wall of the Petri dish.

The liquid culture medium contained chemical reagents shown in Table 2.

TABLE 2

| Reagent | Concentration |
|---|---|
| Dulbecco's modified Eagle's medium | 90% |
| Fetal bovine serum | 10% |
| Penicillin | 30 units/ml |
| Streptomycin | 30 µg/ml |

The plasmid (RTP1S), the plasmid (Rho-myc-Olfr15), and a plasmid (purchased from Evrogen, trade name: pMkate2) coding for a membrane marker were added to the Petri dish, and the HEK293T cells were transfected with these three plasmids by a lipofection method. The liquid culture medium was maintained under an air atmosphere containing 5% $CO_2$ under a temperature of 37 degrees Celsius. In this way, as shown in the uppermost part of FIG. 4, the vessel containing the transformed HEK293 cells and the liquid culture medium was prepared.

(Contact with Chlorpromazine)
Twenty four hours after the transfection, a liquid culture medium containing chlorpromazine was added into the vessel. The chlorpromazine had a concentration of 25 µm/mL. This liquid culture medium also contained the chemical reagents shown in Table 2. In this way, the HEK293 cells were immersed in the liquid culture medium containing chlorpromazine for 20 hours (hereinafter, this time is referred to as "immersion time").

(Exchange of the Liquid Culture Medium)
Subsequently, the liquid culture medium was removed. Then, the liquid culture medium not containing chlorpromazine (see FIG. 2) was added to the vessel. Thus, the liquid culture medium was exchanged.

(Expression of the Olfactory Receptor on the Cell Membrane)
The HEK293T cells were incubated to express the mouse olfactory receptor Olfr15 (SEQ ID NO: 20) on the cell membrane thereof. This mouse olfactory receptor Olfr15 (SEQ ID NO: 20) consists of an amino acid sequence where the N-terminal of the amino acid sequence represented by SEQ ID NO: 19 is modified with the amino acid sequence (SEQ ID NO: 18) including the Rho tag (SEQ ID NO: 10)—the myc epitope tag (SEQ ID NO: 30).

(Evaluation)
Four hours after the exchange of the liquid culture medium, the distribution of the mouse olfactory receptor Olfr15 on the cell membrane was evaluated in accordance with the immunofluorescence technique disclosed in Non Patent Literature 2. For example, the expression rate on the cell membrane and the cell viability rate were calculated in accordance with the following formulas.

(Expression rate on the cell membrane)=(fluorescence intensity on the cell membrane)/(fluorescence intensity of one entire cell)

(Cell viability rate)=(the number of the living cells when the immunofluorescence technique was performed)/(the number of all the cells when the immunofluorescence technique was performed)

For example, the expression rate and the cell viability rate of not less than ten cells were calculated. Then, each of the average value of these rates was calculated. "Expression rate on the cell membrane" and "Cell viability rate" described in Table 3 are the average rates thereof.

Comparative Example 1

An experiment similar to the Example 1 was performed except that a liquid culture medium which did not contain chlorpromazine was added into the vessel. The result is shown in Table 3.

Comparative Example 2

An experiment similar to the Example 1 was performed except that the plasmid (RTP1S) was not used. The result is shown in Table 3.

Comparative Example 3

An experiment similar to the Example 1 was performed except that phenylarsine oxide (1.7 µg/ml) was used instead of chlorpromazine. The result is shown in Table 3.

Comparative Example 4

An experiment similar to the Example 1 was performed except that sucrose (250 mM) was used instead of chlorpromazine. The result is shown in Table 3.

Examples 2-16

Experiments similar to the Example 1 were performed except that the concentration and the immersion time were varied as shown in Table 4. The results are shown in FIG. 4.

TABLE 3

|  | Expression rate on the cell membrane (%) | Cell viability rate (%) |
| --- | --- | --- |
| Example 1 | 28.4 | 11 |
| Comparative Example 1 | 10.0 | 92 |
| Comparative Example 2 | 9.7 | (Not measured) |
| Comparative Example 3 | 8.9 | (Not measured) |
| Comparative Example 4 | 12.5 | (Not measured) |

TABLE 4

|  | Concentration of chlorpromazine (µg/ml) | Immersion time (hour) | Expression rate on the cell membrane (%) | Cell viability rate (%) |
| --- | --- | --- | --- | --- |
| Comparative Example 1 | — | 0 | 10.0 | 92 |
| Example 1 | 25 | 20 | 28.4 | 11 |
| Example 2 | 25 | 0.5 | 15.1 | 89 |
| Example 3 | 25 | 1 | 29.5 | 55 |
| Example 4 | 25 | 2 | 24.0 | 41 |
| Example 5 | 10 | 0.5 | 9.6 | 89 |
| Example 6 | 10 | 1 | 9.9 | 82 |
| Example 7 | 10 | 2 | 19.7 | 84 |
| Example 8 | 10 | 4 | 16.7 | 81 |
| Example 9 | 10 | 9 | 17.4 | 41 |
| Example 10 | 10 | 20 | 19.2 | 50 |
| Example 11 | 5 | 0.5 | 11.8 | 81 |
| Example 12 | 5 | 1 | 8.1 | 88 |
| Example 13 | 5 | 2 | 12.3 | 89 |
| Example 14 | 5 | 4 | 8.5 | 82 |
| Example 15 | 5 | 9 | 11.5 | 79 |
| Example 16 | 5 | 20 | 14.1 | 68 |

As is clear from Table 3, the expression rate of the olfactory receptor Olfr15 on the cell membrane increases when chlorpromazine is added.

A skilled person can choose the concentration of chlorpromazine and the immersion time on the basis of Table 4. For example, a concentration of chlorpromazine can be not less than 10 µg/ml and not more than 25 µg/ml. For example, an immersion time can be not less than 0.5 hours and not more than 20 hours.

INDUSTRIAL APPLICABILITY

The method of the present disclosure can be used in the fabrication of an artificial olfactory device, a compound sensor, and an adsorption film of an odor molecule.

---

What is claimed is:

1. A method for expressing a mouse olfactory receptor 15 (olfr15) on a cell membrane, the method comprising the steps of:
   (a) transfecting a cell with a vector encoding the mouse Olfr15 receptor as set forth in SEQ ID NO: 20 and a receptor transporting protein,
   (b) contacting the transfected cells of step (a) with a culture medium containing chlorpromazine,
   (c) removing the culture medium containing chlorpromazine, and;
   (d) incubating the transfected cell from step (c) in a culture medium which does not contain chlorpromazine to express the mouse Olfr15 on the cell membrane.

2. The method according to claim 1, wherein in step (a), a vector coding for the mouse olfactory receptor Olfr15 and a vector coding for the receptor-transporting protein is used.

3. The method according to claim 1, wherein in step (b), the concentration of the chlorpromazine is not less than 10 µg/ml and not more than 25 µg/ml.

4. The method according to claim 1, wherein the transfected cell is left at rest between step (a) and step (b).

* * * * *